United States Patent [19]

Cohen

[11] 4,049,791
[45] Sept. 20, 1977

[54] PROLONGED ACTING APPETITE SUPPRESSANT AND ANTI-OBESITY COMPOSITIONS CONTAINING AMPHETAMINE ADIPATE, DEXTROAMPHETAMINE ADIPATE, AMPHETAMINE SULFATE AND DEXTROAMPHETAMINE SULFATE AS THE ACTIVE AGENTS

[75] Inventor: Louis Cohen, Yonkers, N.Y.

[73] Assignee: Delco Chemical Company, Inc., Mount Vernon, N.Y.

[21] Appl. No.: 652,526

[22] Filed: Jan. 26, 1976

Related U.S. Application Data

[63] Continuation-in-part of Ser. No. 481,671, June 21, 1974, abandoned.

[51] Int. Cl.² ............... A61K 9/52;; A61K 9/54; A61K 31/135
[52] U.S. Cl. ..................... 424/20; 424/19; 424/21; 424/22; 424/330
[58] Field of Search ................ 424/19–22, 424/325, 330

[56] References Cited

U.S. PATENT DOCUMENTS

| 3,304,230 | 2/1967 | Abramson et al. ............ 424/45 |
| 3,608,063 | 9/1971 | Banker .......................... 424/22 |

OTHER PUBLICATIONS

Stecher et al. Merck Index 8th ed. (1968) pp. 74–75 Amphetamine Sulfate; "Dextro Amphetamine Sulfate".
Chem. Abstracts 70 No. 14394p (1969); 67 No. 67588z (1967); 64 No. 8787a (1966); 54 No. 21508g (1960); 53 No. 17420i (1959); 52 No. 20884e (1958).

*Primary Examiner*—Shep K. Rose
*Attorney, Agent, or Firm*—Jacobs & Jacobs

[57] ABSTRACT

A prolonged acting appetite suppressant and anti-obesity composition in oral administration form which comprises an effective amount of a synergistic combination of amphetamine adipate, dextroamphetamine adipate, amphetamine sulfate and dextroamphetamine sulfate in equal or substantially equal amounts as the active agents in combination with a pharmaceutically acceptable carrier and is useful in suppressing one's appetite and in treating obesity.

11 Claims, No Drawings

PROLONGED ACTING APPETITE SUPPRESSANT AND ANTI-OBESITY COMPOSITIONS CONTAINING AMPHETAMINE ADIPATE, DEXTROAMPHETAMINE ADIPATE, AMPHETAMINE SULFATE AND DEXTROAMPHETAMINE SULFATE AS THE ACTIVE AGENTS

This is a continuation-in-part of application Ser. No. 481,671 filed June 21, 1974, now abandoned.

The present invention is concerned with prolonged-acting appetite suppressant and anit-obesity compositions. More particularly, the present invention is concerned with compositions in oral administration form which comprise an effective amount of a combination of at least two active agents selected from the group consisting of amphetamine adipate, dextroamphetamine adipate, amphetamine sulfate and dextroamphetamine sulfate in combination with a pharmaceutically-acceptable solid vehicle or carrier.

The compositions are preferably in the form of tablets or capsules.

The compositions of the present invention are effective for diminishing the rate of excretion by prolonging blood levels above the minimum effective concentration while avoiding peak concentrations and those side effects which may be encountered with respect to prior known amphetamine preparations. The use of a combination of the active agents set forth above have a stabilizing effect on the enzyme d-amino oxidase thereby prolonging appetite-suppressant effect of amphetamine and dextroamphetamine in the treatment of exogenous obesity while reducing undesired or adverse side effects encountered with amphetamine and dextroamphetamine.

According to one embodiment of the present invention, 10%–75% by weight of the adipate and sulfate of amphetamine or dextroamphetamine is combined with a pharmaceutically acceptable carrier. According to a preferred embodiment of the present invention, an effective amount of a combination of amphetamine adipate, dextroamphetamine adipate, amphetamine sulfate and dextroamphetamine sulfate in substantially equal or equal amounts is combined with a pharmaceutically acceptable carrier. This combination of all four active agents gives the best results with the least side effects and additionally provides a prolonged appetite-suppressant action by incrementally releasing the active ingredients over a period in the order of six to eight hours. It has also been found that when the compositions of the present invention are administered, there are lower excretion rates due to prolongation of the half-life of the amphetamine and/or dextroamphetamine while stabilizing the base enzyme inhibitor d-amino oxidase and reducing adverse effects. It is believed that this is due to the synergism resulting from the combination of the adipate and sulfate of the active agents.

According to another embodiment of the present invention, the active agents are present in equal amounts.

According to another embodiment of the present invention, the composition is in tablet form.

According to another embodiment of the present invention, the composition is in capsule form.

According to another embodiment of the present invention, the composition is in sustained-release capsule form. The active agents in the capsule are in the form of coated seeds which have coatings of different thicknesses or solubilities whereby the active agents are released incrementally over a period of 6 to 8 hours.

According to another embodiment of the present invention, the active agents are a combination of d,l-amphetamine adipate, dextroamphetamine adipate, amphetamine sulfate and dextroamphetamine sulfate in equal amounts.

According to another embodiment of the present invention, the composition is a combination of d,l-amphetamine adipate, dextroamphetamine adipate, amphetamine sulfate and dextroamphetamine sulfate in equal amounts ranging from 1.25 mg per unit dosage.

According to another embodiment of the present invention, the composition is in capsule form in which each active agent is present in each capsule in the amount of 1.25 mg.

According to another embodiment of the present invention, the composition is in tablet form in which each active agent is present in each tablet in the amount of 2.5 mg.

According to another embodiment of the present invention, the composition is in sustained-release capsule form in which each active agent is present in each capsule in the amount of 3.75 mg.

According to another embodiment of the present invention, the composition is in sustained-release capsule form in which each active agent is present in each capsule in the amount of 5 mg.

The compositions may be formulated and prepared in unit dosage form in any manner per se known such as by admixing the active agents with a suitable solid pharmaceutical vehicle of known composition and then compressing the admixture into tablets using standard tabletting machinery. Where it is desired to have a sustained release effect, the pharmaceutical vehicle can be of known nature which breaks down or disintegrates gradually upon ingestion so as to release the active agents over a period of hours such as 6–8 hours. Such compositions of the invention may be filled into capsules such as gelatin capsules and sealed therein. Each such capsule contains a unit dose.

The invention is illustrated by the following nonlimitative examples:

EXAMPLE 1

| Each capsule contains: | |
| --- | --- |
| d,l-amphetamine adipate | 1.25 mg |
| dextroamphetamine adipate | 1.25 mg |
| amphetamine sulfate | 1.25 mg |
| dextroamphetamine sulfate | 1.25 mg |

EXAMPLE 2

| Each tablet contains: | |
| --- | --- |
| d,l-amphetamine adipate | 2.5 mg |
| dextroamphetamine adipate | 2.5 mg |
| amphetamine sulfate | 2.5 mg |
| dextroamphetamine sulfate | 2.5 mg |

EXAMPLE 3

| Each sustained release capsule contains: | |
| --- | --- |
| d,l-amphetamine adipate | 3.75 mg |
| dextroamphetamine adipate | 3.75 mg |
| amphetamine sulfate | 3.75 mg |
| dextroamphetamine sulfate | 3.75 mg |

EXAMPLE 4

| Each sustained release capsule contains: | |
|---|---|
| d,1-amphetamine adipate | 5 mg |
| dextroamphetamine adipate | 5 mg |
| amphetamine sulfate | 5 mg |
| dextroamphetamine sulfate | 5 mg |

In practice, a batch of 600,000 capsules is prepared from nonpareil seeds which are wet with No. 3 confectionery glaze, dried and wet with No. 6 confectionery glaze until the nonpareil seeds are built up to desired size with a plurality of coatings which may, if desired, be alternated with a dusting barrier coating of talc or the like between succeeding layers. The resulting seeds are then compressed into capsules using conventional machinery. The capsules are formulated to give a prolonged release of active anti-obesity agents over a period of 6–8 hours, the active anti-obesity agents being used preferably in powder form in the amount of 2.5 kilos per batch and dusted on the nonpareil seeds. As the seeds are built up they are tested from time to time to ensure the release time of 6–8 hours.

The foregoing is intended as illustrative and not as limitative since within the scope of the appended claims various modifications can be made without departing from the invention. The active agents may be used in any combination of two or more or mixture thereof to obtain prolonged appetite suppressant action, the best mode being equal or substantially equal amounts of all four active substances and wherein the proportion of the total of 5–20 mg is determined according to the patient or subject and the extent of the obesity and other known factors such as age, blood pressure, etc. The synergism referred to above occurs when at least one of the active agents is an adipate and at least one of the active agents is a sulfate.

Examples 5 to 8 illustrate the 5, 10, 15 and 20 mg tablets which are preferred specific embodiments of the present invention:

EXAMPLE 5

5 mg tablet

| Each tablet contains: | | |
|---|---|---|
| dextroamphetamine adipate | 1.25 | mg |
| amphetamine adipate | 1.25 | mg |
| dextroamphetamine sulfate, USP | 1.25 | mg |
| amphetamine sulfate | 1.25 | mg |
| Avicel | 29.25 | mg |
| lactose, USP | 246.05 | mg |
| stearic acid, USP | 5.9 | mg |
| magnesium stearate, USP | 2.95 | mg |
| Cab-O-Sil | 2.95 | mg |
| FD&C Blue No. 1, Lake | 0.2 | mg |

EXAMPLE 6

10 mg tablet

| Each tablet contains: | | |
|---|---|---|
| dextroamphetamine adipate | 2.5 | mg |
| amphetamine adipate | 2.5 | mg |
| dextroamphetamine sulfate, USP | 2.5 | mg |
| amphetamine sulfate, NF | 2.5 | mg |
| Avicel | 29.25 | mg |
| lactose, USP | 240.83 | mg |
| stearic acid, USP | 5.9 | mg |
| magnesium stearate, USP | 2.95 | mg |
| Cab-O-Sil | 2.95 | mg |
| FD&C Blue No. 1, Lake | 0.02 | mg |
| FD&C Red No. 2, Lake | 0.1 | mg |
| FD&C Red No. 3, Lake | 0.1 | mg |

EXAMPLE 7

15 mg tablets

| Each tablet contains: | | |
|---|---|---|
| dextroamphetamine adipate | 3.75 | mg |
| amphetamine adipate | 3.75 | mg |
| dextroamphetamine sulfate, USP | 3.75 | mg |
| amphetamine sulfate, NF | 3.75 | mg |
| Avicel | 29.25 | mg |
| lactose, USP | 235.48 | mg |
| stearic acid, USP | 5.9 | mg |
| magnesium stearate, USP | 2.95 | mg |
| Cab-O-Sil | 2.95 | mg |
| FD&C Yellow No. 6, Lake | 0.35 | mg |
| FD&C Red No. 3, Lake | 0.02 | mg |

EXAMPLE 8

20 mg tablets

| Each tablet contains: | | |
|---|---|---|
| dextroamphetamine adipate | 5.0 | mg |
| amphetamine adipate | 5.0 | mg |
| dextroamphetamine sulfate, USP | 5.0 | mg |
| amphetamine sulfate, NF | 5.0 | mg |
| Avicel | 39.0 | mg |
| lactose, USP | 314.35 | mg |
| stearic acid, USP | 7.66 | mg |
| magnesium stearate, USP | 3.97 | mg |
| Cab-O-Sil | 3.97 | mg |
| FD&C Yellow No. 5, Lake | 0.2 | mg |

Capsules and tablets comprising equal amounts of the four active ingredients formulated into capsules and tablets were tested in a double-blind parallel study of 60 people, 53 of whom were female and 7 of whom were male. Of the 60 subjects, about one third were in the 20s with the remainder evenly distributed in the 30–50 year old age bracket. The subjects were moderately overweight at the beginning of the test, averaging 30–40% based on ideal weight tables.

The duration of the tests was 8 weeks and, in all, 8 subjects dropped out prior to completing at least 5 weeks of the therapy. About one fourth of all the subjects obtained a marked loss of weight during the course of the tests, that is, more than 10 pounds of weight loss. 15% obtained a slight weight loss, that is less than 5 pounds. This percentage, however, obtained approximately the same weight loss whether the subjects received the compositions of the present invention or placebos. However, 37.5% of the subjects which were treated with compositions of the present invention demonstrated a moderate weight loss as compared to only 10% of the subjects which received placebos.

Thus, the compositions of the present invention have clearly demonstrated significant utility in the appetite-suppressant and anti-obesity area.

What is claimed is:

1. The composition in which each dosage unit consists of, per 5 mg of active agent, a synergistic combination of:

| d,1-amphetamine adipate | 1.25 mg |
|---|---|
| dextroamphetamine adipate | 1.25 mg |
| amphetamine sulfate | 1.25 mg |
| dextroamphetamine sulfate | 1.25 mg. |

2. The composition of claim 1 in which each dosage unit consists of 10 mg of active agent as a synergistic combination of:

| | |
|---|---|
| d,l-amphetamine adipate | 2.5 mg |
| dextroamphetamine adipate | 2.5 mg |
| amphetamine sulfate | 2.5 mg |
| dextroamphetamine sulfate | 2.5 mg. |

3. The composition of claim 1 in which each dosage unit consists of 15 mg of active agent as a synergistic combination of:

| | |
|---|---|
| d,l-amphetamine adipate | 3.75 mg |
| dextroamphetamine adipate | 3.75 mg |
| amphetamine sulfate | 3.75 mg |
| dextroamphetamine sulfate | 3.75 mg. |

4. The composition of claim 1 in which each dosage unit consists of 20 mg of active agent as a synergistic combination of:

| | |
|---|---|
| d,l-amphetamine adipate | 5 mg |
| dextroamphetamine adipate | 5 mg |
| amphetamine sulfate | 5 mg |
| dextroamphetamine sulfate | 5 mg. |

5. The composition according to claim 1 which comprises a tablet containing 5 mg of active agent, which tablet consists of:

| | |
|---|---|
| dextroamphetamine adipate | 1.25 mg |
| amphetamine adipate | 1.25 mg |
| dextroamphetamine sulfate, USP | 1.25 mg |
| amphetamine sulfate | 1.25 mg. |

6. A composition according to claim 1 which is in unit dosage tablet form.

7. A composition according to claim 1 wherein the active agents in the capsule are in the form of coated seeds which have coatings of different thicknesses or solubilities whereby the active agents are released incrementally over a period of 6 to 8 hours.

8. A composition according to claim 1 in capsule form in which each active agent is present in each capsule in the amount of 1.25 mg.

9. A composition according to claim 2 in tablet form in which each active agent is present in each tablet in the amount of 2.5 mg.

10. A composition according to claim 3 in sustained release form in capsules in which each active agent is present in each capsule in the amount of 3.75 mg.

11. A composition according to claim 4 in sustained release form in capsules in which each active agent is present in each capsule in the amount of 5 mg.

* * * * *